United States Patent
Berklund et al.

(10) Patent No.: US 8,276,603 B2
(45) Date of Patent: Oct. 2, 2012

(54) MEDICAL EQUIPMENT WASHER SYSTEM AND METHOD

(75) Inventors: Thomas R. Berklund, Wisconsin Rapids, WI (US); Keith Roepke, Chesterfield, MO (US)

(73) Assignee: Stat Medical Systems, L.L.C., St. Louis, MO (US)

( * ) Notice: Subject to any disclaimer, the term of this patent is extended or adjusted under 35 U.S.C. 154(b) by 426 days.

(21) Appl. No.: 11/704,721

(22) Filed: Feb. 9, 2007

(65) Prior Publication Data

US 2008/0190460 A1    Aug. 14, 2008

(51) Int. Cl.
- *B08B 3/00* (2006.01)
- *B08B 3/12* (2006.01)
- *B08B 6/00* (2006.01)

(52) U.S. Cl. ........ 134/123; 134/172; 134/173; 134/174; 134/176; 134/178; 134/179; 134/184; 134/186; 134/198; 134/199; 134/200

(58) Field of Classification Search .................. 134/123, 134/172, 173, 174, 176, 178, 179, 184, 186, 134/198, 199, 200
See application file for complete search history.

(56) References Cited

U.S. PATENT DOCUMENTS

| | | | |
|---|---|---|---|
| 2,981,266 A | | 4/1961 | Tamburri |
| 3,736,948 A | * | 6/1973 | Crosswhite .................. 134/95.2 |
| 4,279,263 A | * | 7/1981 | Pulliam ......................... 134/111 |
| 4,452,263 A | * | 6/1984 | McClure ......................... 134/45 |
| 5,041,220 A | * | 8/1991 | Lee et al. .................... 210/321.8 |
| 5,133,375 A | * | 7/1992 | Schinzing et al. ............ 134/123 |
| 5,285,802 A | * | 2/1994 | Soderquist .................... 134/123 |
| 5,622,196 A | | 4/1997 | Luongo |
| 5,939,974 A | * | 8/1999 | Heagle et al. ............ 340/286.09 |
| 5,993,739 A | * | 11/1999 | Lyon ............................... 422/31 |
| 6,959,714 B1 | | 11/2005 | Hakansson et al. |

FOREIGN PATENT DOCUMENTS

| | | | |
|---|---|---|---|
| JP | 09328778 A | * | 12/1997 |
| WO | WO 2007014565 A1 | * | 2/2007 |

OTHER PUBLICATIONS

Aqua Phase AQ-4000 Operating Manual, Jan. 20, 2005, <http://www.medwashers.com/Manual%20AQ-4000%20050120.pdf>.*
Aqua Phase Set Up Instructions, Jan. 28, 2005, <http://www.medwashers.com/AQ%20Setup%20Instructions%20050128.pdf>.*
AQ-4000 Design Features, circa 2006, <http://www.medwashers.com/Aqua%20Phase%204000.htm>.*
Aqua Phase Update, vol. 4, Issue 1, Spring 1999 (Aqua Phase Newsletter) for details on product spec's, refer to http://www.medwashers.com/Aqua/%20Phase%20Options.htm.
PCT/US2008/053073 International Search Report and Written Opinion dated Jun. 20, 2008, 10 pages.

* cited by examiner

*Primary Examiner* — Michael Barr
*Assistant Examiner* — Charles W Kling
(74) *Attorney, Agent, or Firm* — Michael Best & Friedrich LLP

(57) ABSTRACT

Embodiments of the invention provide a system and method of cleaning and/or disinfecting medical equipment. A medical equipment washer system can include an enclosure that receives and substantially surrounds the medical equipment and one or more spray assemblies positioned inside the enclosure. The spray assemblies can automatically emit fluid to clean and/or disinfect the medical equipment. In some embodiments, spray arms of the spray assemblies can oscillate while jets emit fluid.

36 Claims, 20 Drawing Sheets

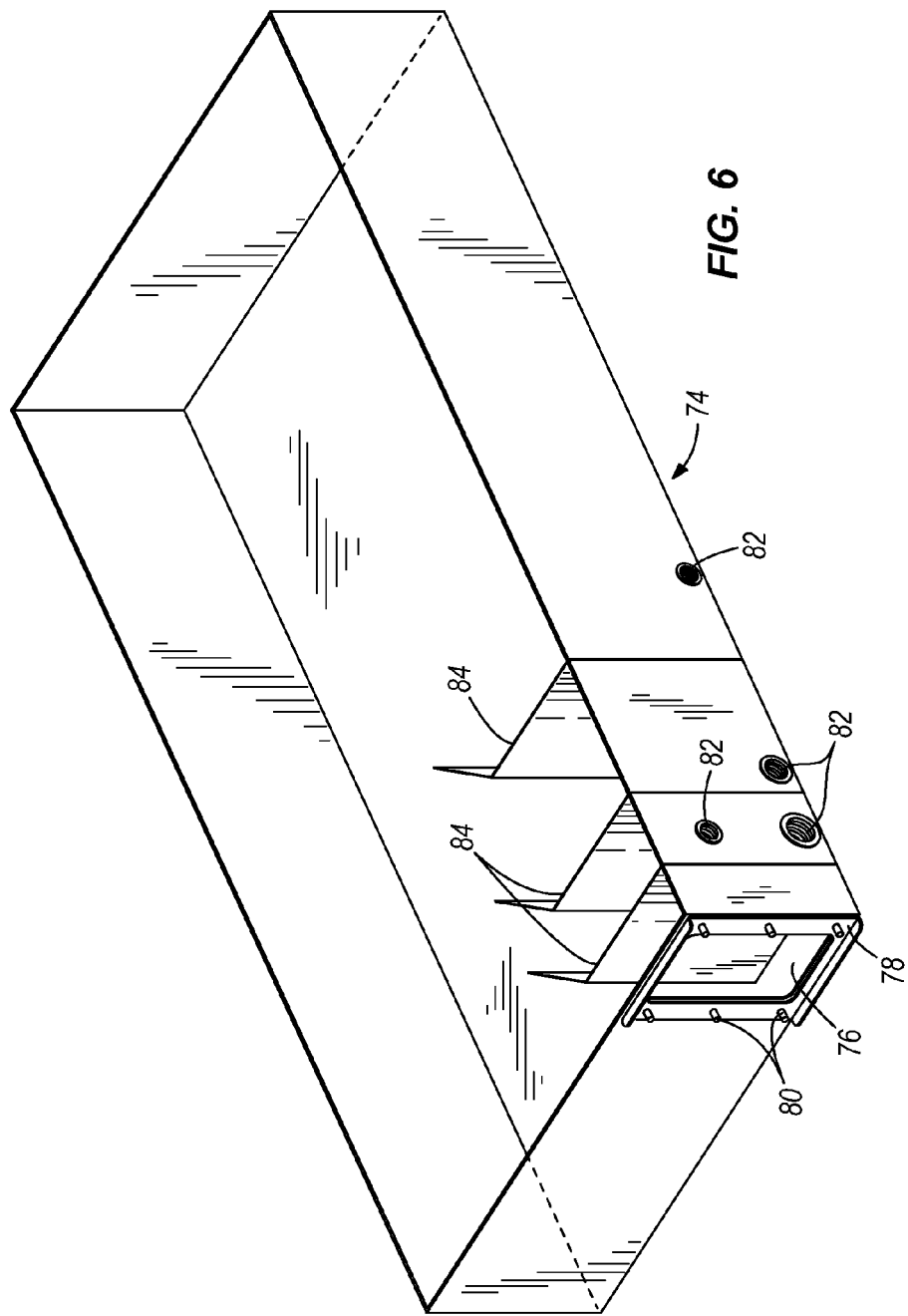

FIG. 13

| Steps | | Pumps | | | Motors | | Pumps | | Valves | | | | | | Wait For |
|---|---|---|---|---|---|---|---|---|---|---|---|---|---|---|---|
| | | Main | Transfer | Disinfect | Oscillating Spray Arms | | Detergent | Rinse Aid | Fresh Water | Transfer Water | Large Water | Drain | Disinfectant Spray Arms | Tank Spray | |
| | | M1 | M2 | M3 | M4 | M5 | M6 | M7 | SV1 | SV2 | SV3 | SV4 | SV5 | SV6 | |
| 1 | Fill SWT | | | | | | | | X | | | | | | LS5 |
| 2 | Start Filling MWT | | X | | | | | | | X | | | | | Time Delay |
| 3 | Add Detergent | | X | | | | X | | | X | | | | | Timed Dosage |
| 4 | Filling MWT | | O | | | | | | | O | | | | | LS2 |
| 5 | Add De-Liming Agent | | | | | | | | | | | | | | Cycle Start PB |
| 6 | Tank Spray | X | | | | | | | | | | | | | Tank Spray Timer |
| 7 | Clean | X | | | X | X | | | | | | | | | Wash Timer |
| 8 | Complete Drain MWT | X | | | | | | | | | X | | | | LS1 |
| 9 | Start Filling MWT | | X | | | | | | | X | | | | | Time Delay |
| 10 | Add Rinse Aid | | X | | | | | X | | X | | | | | Timed Dosage |
| 11 | Filling MWT | | O | | | | | | | O | | | | | LS2 |
| 12 | Rinse | X | | | X | | | | | | X | | | | Rinse Timer |
| 13 | Partial Drain MWT | X | | | | | | | | | | X | | | Drain Timer |
| 14 | Disinfect | | | X | | | | | | | | X | X | | Disinfect Timer or LS2? |
| 15 | Complete Drain MWT | X | | | | | | | O | | | X | | | LS1 |
| 16 | Start Drain SWT | | X | | | | | | | X | | X | | | LS2 |
| 17 | Complete Drain MWT | X | X | | | | | | | X | | X | | | LS1 & LS3 |
| 18 | Partial Fill SWT | | | | | | | | X | | | | | | LS4 |
| 19 | Add Virex to SWT | | | X | | | | | | | | | O | | Virex Timer |
| 20 | Start Draining SWT to MWT | | X | | | | | | | X | | | | | Time Delay |
| 21 | Add Detergent | | X | | | | X | | | X | | | | | Timed Dosage |
| 22 | Finish Draining SWT | | O | | | | | | | O | | | | | LS3 |
| 23 | Clean Machine | X | | | X | X | | | | | X | | | | Shutdown Timer |
| 24 | Complete Drain MWT | X | | | | | | | O | | | X | | | LS1 |
| 25 | Cycle Complete | | | | | | | | | | | | | | |

MEDICAL EQUIPMENT WASHER SYSTEM AND METHOD

BACKGROUND OF THE INVENTION

Infection control has always been an important issue for hospitals. Now the landscape is changing and it is pushing this issue to the forefront. Hospital-acquired, drug-resistant infections are increasing dramatically. The emergence of drug-resistant infections has only compounded this issue.

In many states, hospitals are already required to publish their "hospital acquired" infection rates. In 2008, this will be a national requirement. Both health maintenance organizations and the public are seeking out hospitals with the best infection control. In addition, the primary hospital accreditation group, the Joint Commission on the Accreditation of Hospital Organizations (JCAHO), has recently been imposing new standards on hospitals requiring them to record when, where, and by whom each piece of equipment was cleaned and disinfected.

Keeping equipment clean can dramatically lower the incidence of infections. Presently, there is little equipment to wash high touch, intimate contact items, particularly hospital stretchers and intravenous (IV) poles. Often, hospital stretchers may get only a cursory alcohol wipe down, while many IV poles never get cleaned at all. Health care industry "timed tasking" standards say it takes one hour and ten minutes to properly hand clean a hospital stretcher.

One medical equipment washer presently on the market appears to be an adapted piece of dairy cleaning equipment. It is ineffective, very slow, and has no recording or documentation capabilities. In addition, each new location requires the equipment to be individually designed and configured, making mass production impractical. In addition, this equipment has mild steel components that rust and slip joints that leak.

SUMMARY OF THE INVENTION

In light of the above, some embodiments of the invention provide a medical equipment washer for cleaning and/or disinfecting medical equipment. The medical equipment washer can include an enclosure that receives and substantially surrounds the medical equipment and one or more spray assemblies positioned inside the enclosure. The spray assemblies can automatically emit fluid to clean and/or disinfect the medical equipment. In some embodiments, the spray assemblies can oscillate while jets emit fluid.

One embodiment of a method of the invention includes cleaning and/or disinfecting medical equipment by enclosing the medical equipment and automatically performing a wash cycle by spraying fluid to clean and/or disinfect the medical equipment. In some embodiments, the method includes oscillating one or more spray arms and emitting fluid from jets.

BRIEF DESCRIPTION OF THE DRAWINGS

FIG. 6 is a perspective view of a residual tank according to one embodiment of the invention for use with the system of FIG. 1.

FIG. 13 is a spreadsheet of cycle steps performed by the control circuit of FIG. 9 for use with the system of FIG. 1.

DETAILED DESCRIPTION OF THE INVENTION

Figure 1:
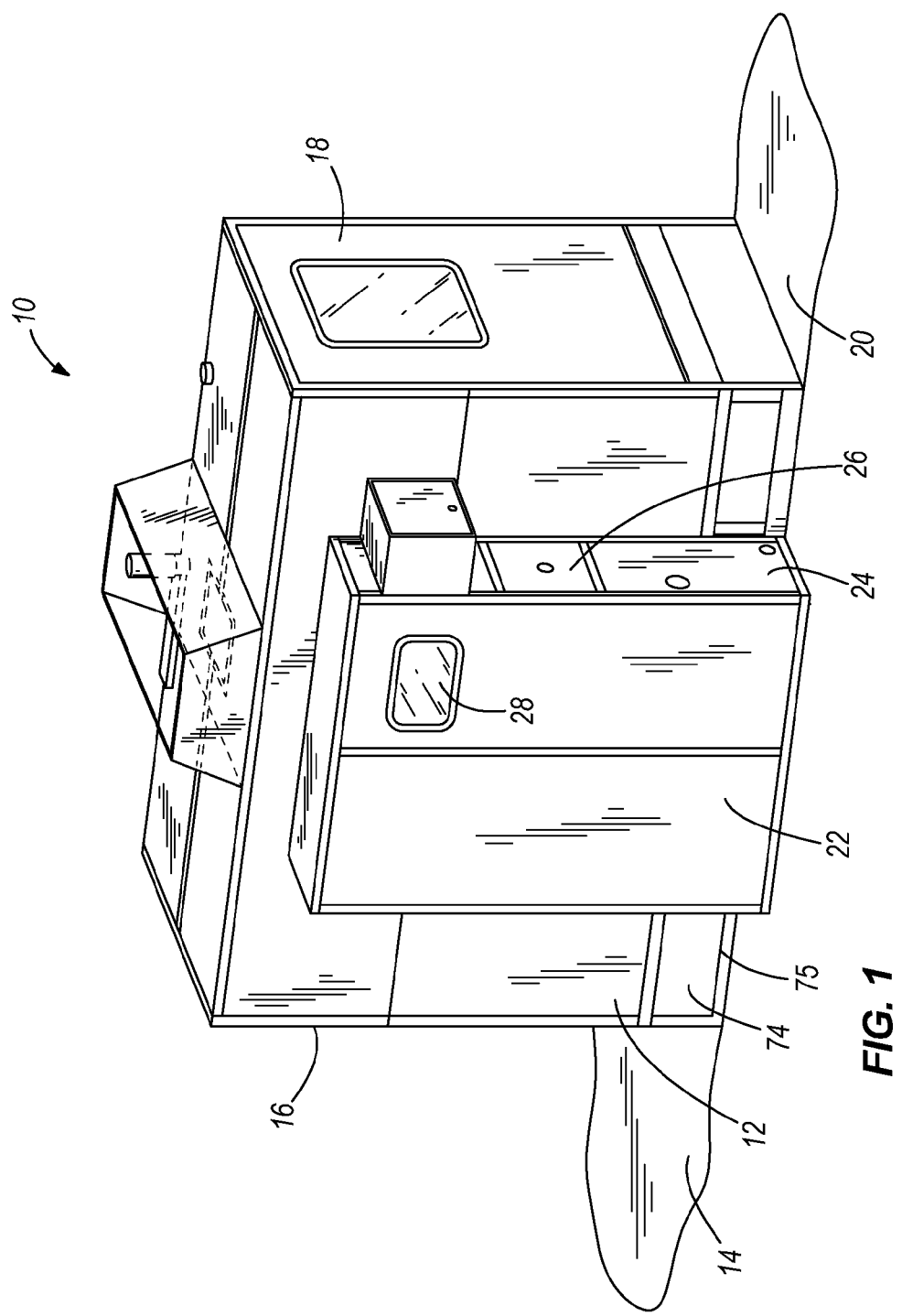
FIG. 1 is a perspective view of a medical equipment washer system according to one embodiment of the invention.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limited. The use of "including," "comprising" or "having" and variations thereof herein is meant to encompass the items listed thereafter and equivalents thereof as well as additional items. The terms "mounted," "connected" and "coupled" are used broadly and encompass both direct and indirect mounting, connecting and coupling. Further, "connected" and "coupled" are not restricted to physical or mechanical connections or couplings, and can include electrical connections or couplings, whether direct or indirect.

In addition, embodiments of the invention include both hardware and electronic components or modules that, for purposes of discussion, may be illustrated and described as if the majority of the components were implemented solely in hardware. However, one of ordinary skill in the art, and based on a reading of this detailed description, would recognize that, in at least one embodiment, the electronic based aspects of the invention may be implemented in software. As such, it should be noted that a plurality of hardware and software based devices, as well as a plurality of different structural components may be utilized to implement the invention. Furthermore, and as described in subsequent paragraphs, the specific mechanical configurations illustrated in the drawings are intended to exemplify embodiments of the invention and that other alternative mechanical configurations are possible.

FIG. 1 illustrates a medical equipment washer system 10 according to one embodiment of the invention. The washer system 10 can be used to perform a wash cycle to clean and/or disinfect various types of medical equipment (not shown), including, for example, a stretcher, an intravenous (IV) pole, a bed, a wheelchair, a linen cart, a biological hazard cart, and a cushion (such as a ROHO® cushion). The washer system 10 can wash medical equipment from, for example, a hospital, a public health facility, a military field hospital, emergency medical services, a biological terror event, or a mobile unit.

As used herein and in the appended claims, the term "wash" includes only cleaning, only disinfecting, or both cleaning and disinfecting. Similarly, the term "washer" includes equipment that performs only cleaning, only disinfecting, or both cleaning and disinfecting.

As shown in FIG. 1, the washer system 10 can include an enclosure 12, a first ramp 14, a first door 16, a second door 18, a second ramp 20, a pump cabinet 22, a primary fluid tank 24, one or more secondary fluid tanks 26, and a control panel 28.

Each piece of medical equipment can be rolled or pushed up the first ramp 14 and into the enclosure 12. In some embodiments, the ramps 14 and 20 can be curved to allow loading of stretchers without damaging the hydraulic undercarriage of the stretchers. Also, due to the two doors 16 and 18, the medical equipment can be moved in a single direction through the enclosure 12. In some embodiments, the control panel 28 can be centrally located between the first door 16 and the second door 18. In addition, due in part to the location of the doors 16 and 18 and the control panel 28, the washer system 10 can be universally located in any suitable position within a hospital building or other facility. As a result, the washer system 10 can be produced using a mass assembly line, rather than each washer system 10 being individually designed for its intended location.

Certain pieces of medical equipment can be positioned on equipment racks inside of the enclosure 12. For example, one embodiment of an equipment rack can support several IV poles. In addition, one embodiment of an equipment rack can allow cushions to be folded over a support so that spaces between the cushions can be opened to receive cleaning and/or disinfecting fluid. A wash cycle can be performed while the medical equipment is substantially surrounded in the enclosure 12. The washed medical equipment can then be rolled or pushed out the second door 18 and down the second ramp 20. In some embodiments, the enclosure 12 can have a maximum width of about four feet in order to fit through a standard hospital door.

Figure 2A:
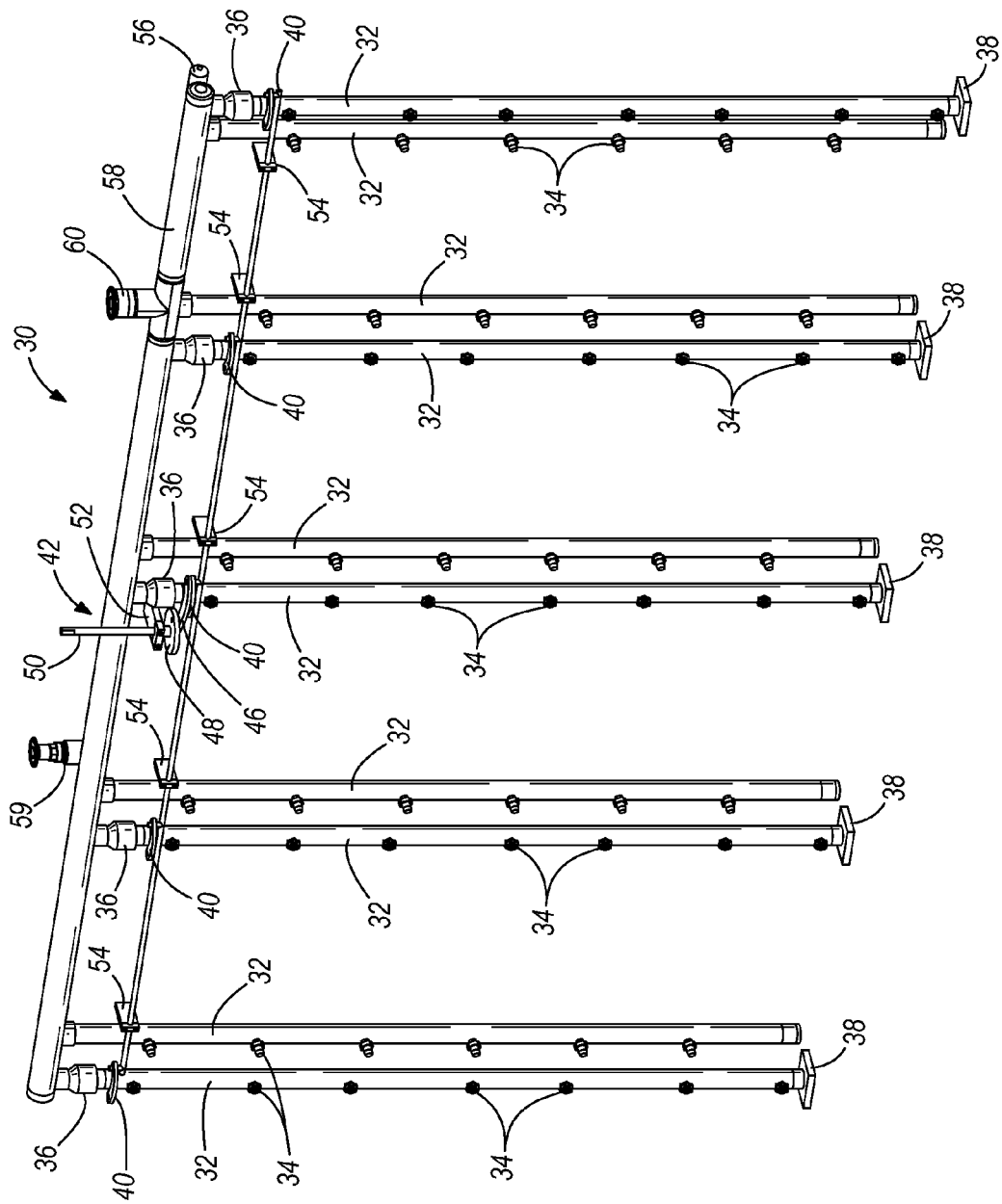
FIGS. 2A and 2B are front and back perspective views, respectively, of a spray assembly according to one embodiment of the invention for use with the system of FIG. 1.
Figure 2B:
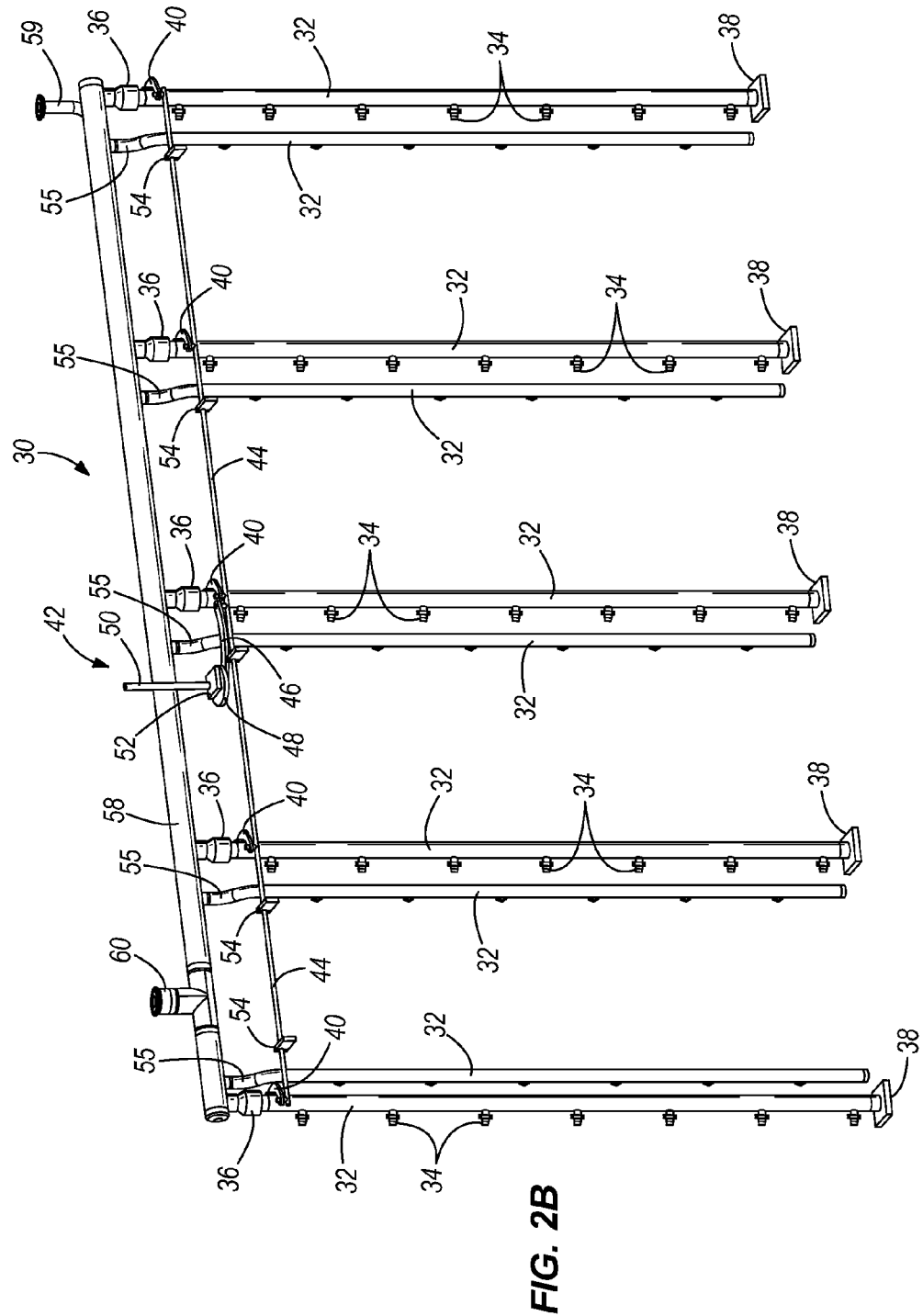
Figure 3:
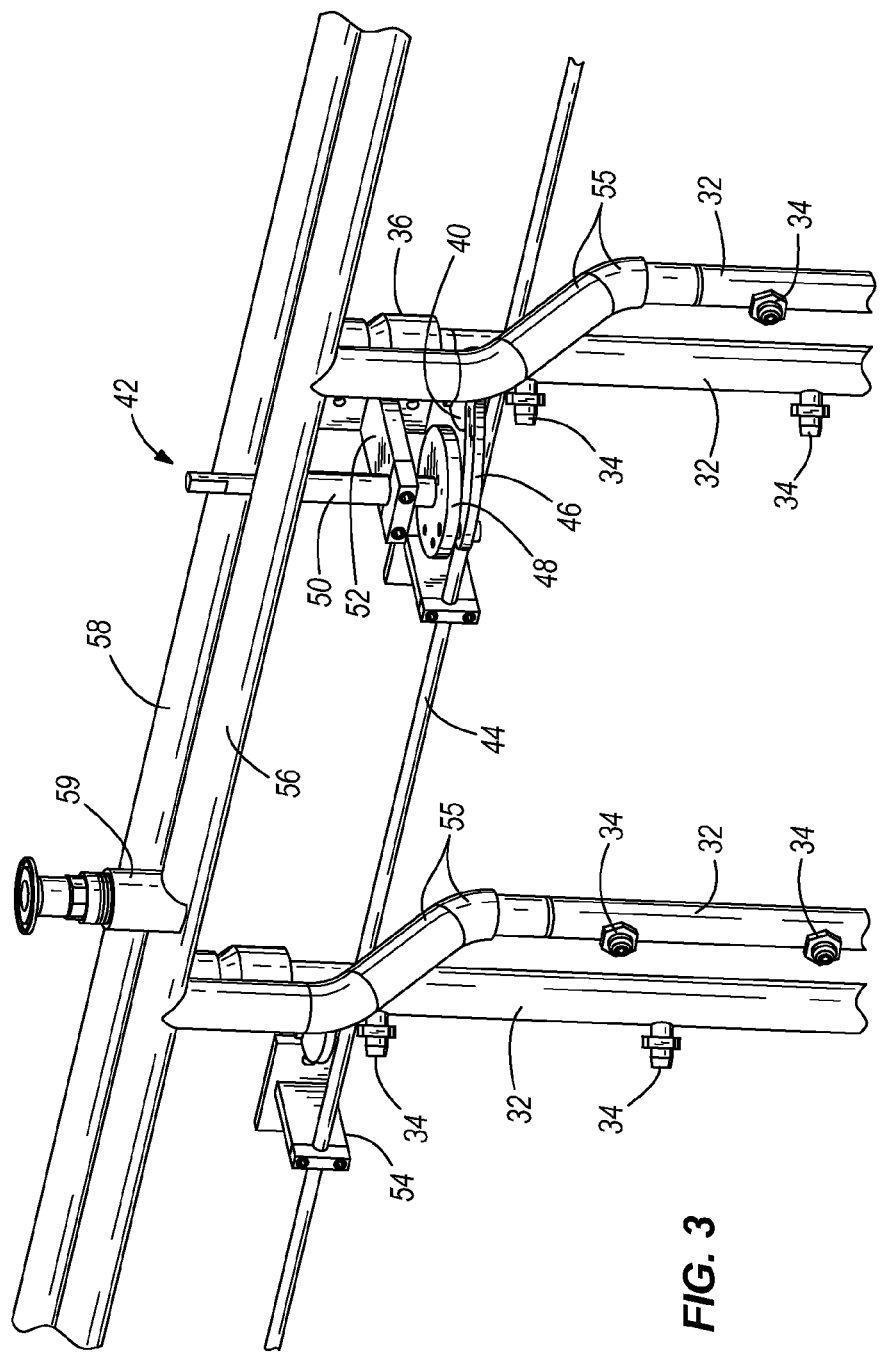
FIG. 3 is another front perspective view of the spray assembly of FIGS. 2A and 2B.

FIGS. 2A, 2B, and 3 illustrate a spray assembly 30 that can be positioned inside the enclosure 12. In some embodiments, the washer system 10 can include two spray assemblies 30 positioned within the enclosure 12, one on each side between the first door 16 and the second door 18. The spray assembly 30 can include one or more spray arms 32. In some embodiments, one spray assembly 30 can include ten spray arms. In some embodiments, the spray arms 32 can be vertically aligned. The spray arms 32 can each include one or more jets 34. For example, in some embodiments, each spray arm 32 can include six or more jets 34.

One or more of the spray arms 32 can be rotatably coupled to a swivel joint 36, for example, at a top end of the spray arm 32. The spray arms 32 that are coupled to the swivel joints 36 can also be rotatably coupled to pivot blocks 38, for example, at a bottom end of the spray arms 32. The spray arms 32 (that are coupled to the swivel joints 36 and the pivot blocks 38) can oscillate in order to create a spray pattern within the enclosure 12. In some embodiments, the oscillating spray arms 32 emit only cleaning fluid. In some embodiments, the oscillating spray arms 32 can include pipes having a diameter of about 1¼ inches. In some embodiments, the jets 34 coupled to the oscillating spray arms 32 can have a capacity of about 2.5 gallons per minute. The oscillating spray arms 32 can each be coupled to a curved arm 40. Each curved arm 40 can be coupled to a drive rod assembly 42 in order to drive the oscillating spray arms 32 substantially in unison.

Figure 4:
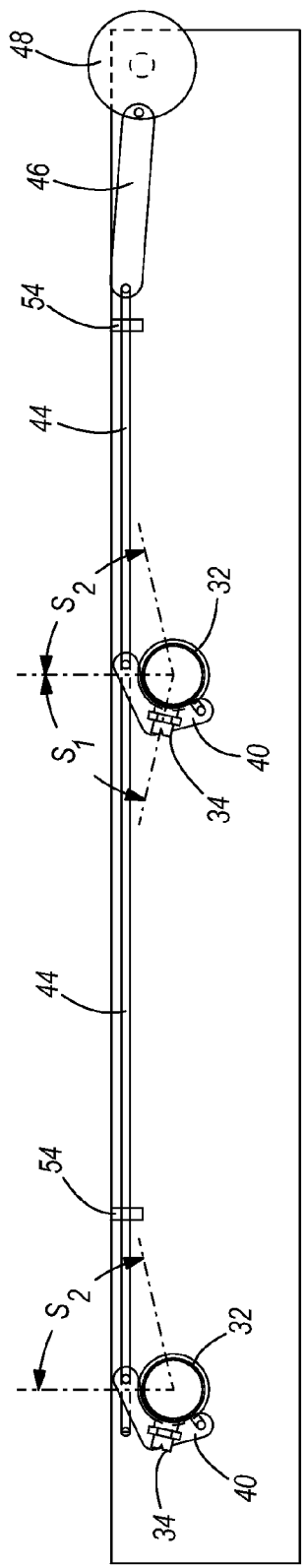
FIG. 4 is a top view of the spray assembly of FIGS. 2A, 2B, and 3 illustrating a spray pattern of one embodiment of the invention.

As shown in FIG. 3, the drive rod assembly 42 can include a drive rod 44, a push bar 46, a drive cam 48, a drive shaft 50, a shaft bracket 52, and drive rod brackets 54. The drive shaft 50 can be coupled to a motor (not shown) in order to rotate the drive cam 48. The drive cam 48 can be coupled to the push bar 46 in an offset manner, for example, by being coupled to the drive cam 48 near the periphery of a bottom circular face of the drive cam 48. The end of the push bar 46 coupled to the drive rod 44 can cause the drive rod 44 to translate with respect to the drive rod brackets 54, which can be substantially stationary. As the push bar 46 causes the drive rod 44 to translate, the drive rod 44 can cause each one of the curved arms 40 to move along a curved path. Each curved arm 40 coupled to each spray arm 32 can cause the spray arms 32 to oscillate, causing the jets 34 coupled to the spray arms 32 to create a spray pattern, as shown in FIG. 4. As the drive rod 44 moves in one direction, the jets 34 can create a first spray pattern having a first spray angle $S_1$ (e.g., about 77 degrees). As the drive rod 44 moves in the opposite direction, the jets 34 can create a second spray pattern having a second angle $S_2$ (e.g., also about 77 degrees). As a result, in one embodiment, each oscillating jet 34 can move about 154 degrees with one full rotation of the drive cam 48.

One or more of the spray arms 32 can be substantially stationary, causing the jets 34 to spray in a pattern dictated by the nozzle and/or discharge orifice of the jets 34. In some embodiments, the stationary spray arms 32 can emit only disinfectant fluid. In some embodiments, the stationary spray arms 32 can having a diameter of about one inch. In some embodiments, the stationary spray arms 32 can be coupled to jets 34 including conical spray nozzles having a capacity of about 4 gallons per hour. As shown in FIG. 3, in some embodiments, the stationary spray arms 32 can be coupled to one or more fittings 55 to create a curve at an upper end of each spray arm 32. In some embodiments, the stationary spray arms 32 can each be coupled to a first supply tube 56, while the oscillating spray arms 32 can be coupled to a second supply tube 58 via the swivel joints 36 and other suitable fittings. As shown in FIG. 3, the first supply tube 56 can be coupled to a source of fluid by tubing and a fitting 59. As shown in FIGS. 2A and 2B, the second supply tube 58 can be coupled to a source of fluid by tubing and a T-shaped connector 60.

Figure 5A:
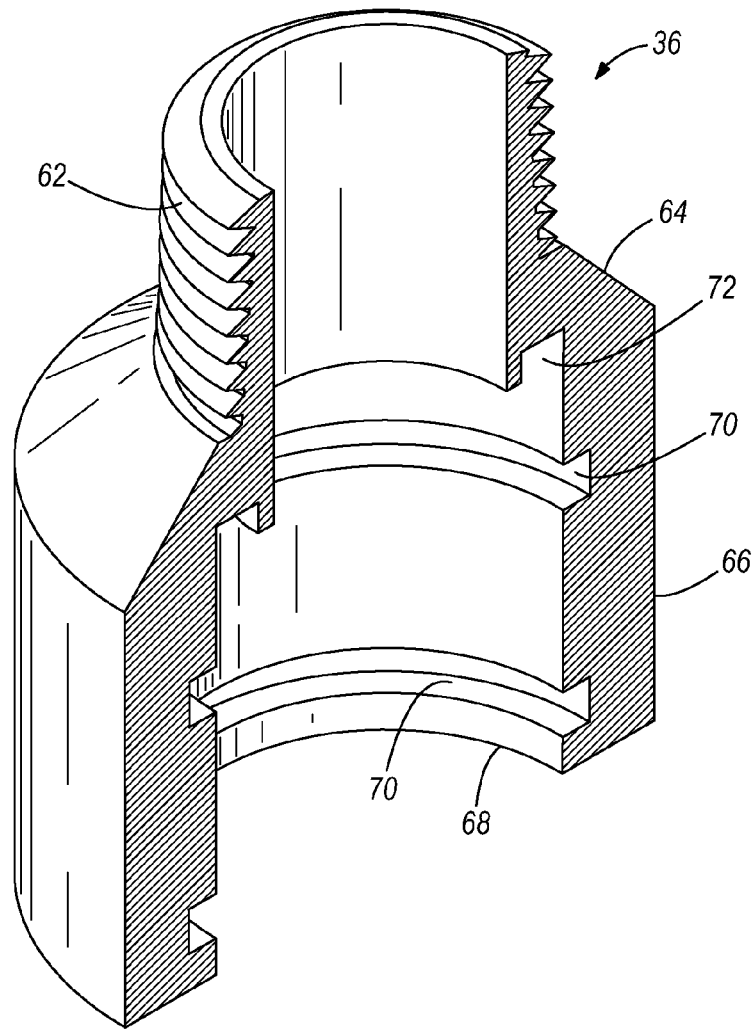
FIGS. 5A-5D are a cross-sectional perspective view, a side view, a cross-sectional side view, and a top view of a pipe swivel for use with the spray assembly of FIGS. 2A, 2B, and 3.
Figure 5C:
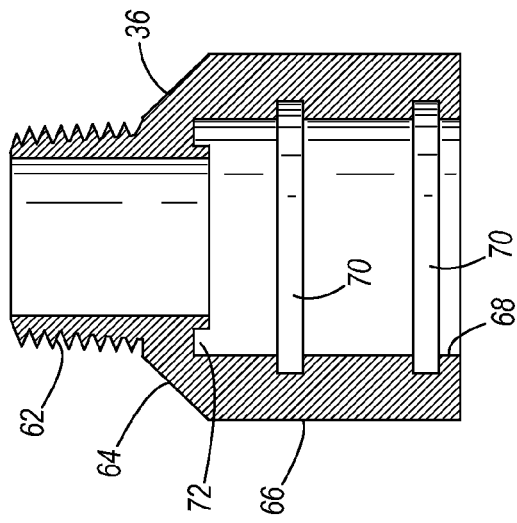
Figure 5D:
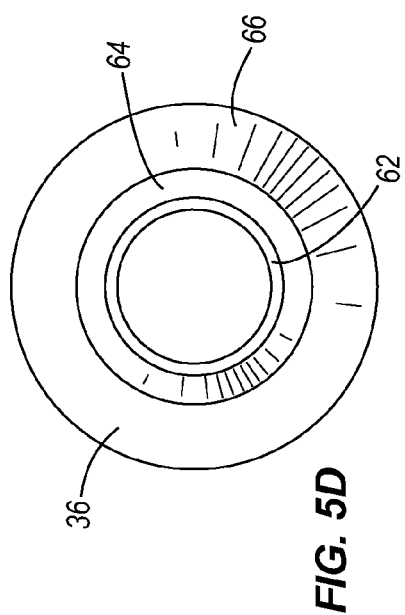
Figure 5B:
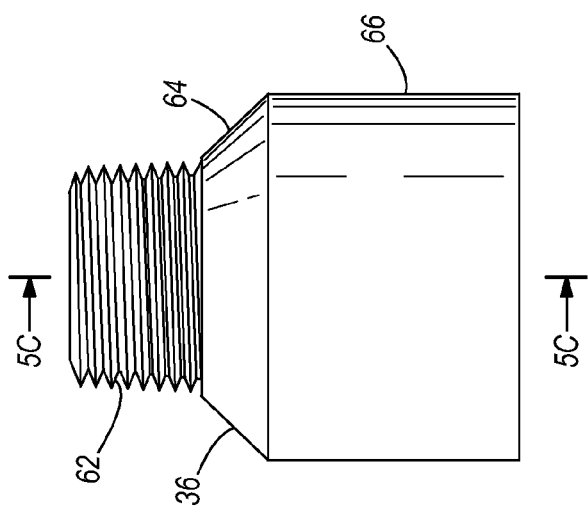

FIGS. 5A-5D illustrate one embodiment of the swivel joint 36 for use with the spray assembly 30. The swivel joint 36 can include a threaded portion 62 that can be used to couple the swivel joint 36 in a fixed manner to suitable fittings and the second supply tube 58. The swivel joint 36 can include an angled portion 64 and a body portion 66. An interior surface 68 of the body portion 66 can include one or more side annular grooves 70 (e.g., grooves having a 0.1 inch width). Each side annular groove 70 can receive a seal, such as an O-ring (not shown). The upper portion of the spray arm 32 can be received by the interior surface 68 of the body portion 66 in order to be seated within the side annular grooves 70. As shown in FIGS. 5A and 5C, the swivel joint 36 can also include a top annular groove 72, which can receive an upper annular surface of the spray arm 32. The top annular groove 72 can reduce water pressure on the O-rings.

In addition or in place of some of the spray arms 32, some embodiments of the washer system 10 can include one or more corner-mounted spray arms (not shown). The corner-mounted spray arms can emit fluid toward the front and back ends of stretchers. In one embodiment, the washer system 10 can include four disinfectant spray arms at the four corners of the enclosure 12 in order to substantially cover the ends of hospital stretchers and the underside base of IV poles.

In some embodiments, the enclosure 12, the spray arms 32, and/or other components of the washer system 10 can be constructed of a material including stainless steel.

FIG. 6 illustrates one embodiment of a secondary or auxiliary tank 74 for use with the washer system 10. The secondary tank 74 can receive water from the hospital's water supply or another suitable water supply. In some embodiments, the secondary tank 74 can also receive disinfectant during certain stages of the wash cycle. The secondary tank 74 can be generally rectangular in shape with a width substantially smaller than its overall height. The secondary tank 74 can include a rectangular opening 76 on one end near the corner. The rectangular opening 76 can be surrounded by a flange 78 with fasteners 80. The secondary tank 74 can include pipe fittings 82 on one side. The secondary tank 74 can include baffles 84 to direct fluid in its interior and in order to combat turbulence so that sensors placed adjacent to tank walls (e.g., sensors reading through plastic windows) can make accurate readings of the fluid level within the secondary tank 74. In some embodiments of the washer system 10, the secondary tank 74 can be positioned in an opening 75 (as shown in FIG. 1) under the enclosure 12. In some embodiments, two or more secondary tanks 74 can be used in the washer system 10 in order to increase the wash capacity of the washer system 10. For example, two or more secondary tanks 74 can be coupled together in series by a 2 inch diameter pipe fitting. One or more solenoids (not shown) can be used to control the flow of supply water to and/or between the secondary tanks 74.

Figure 7:
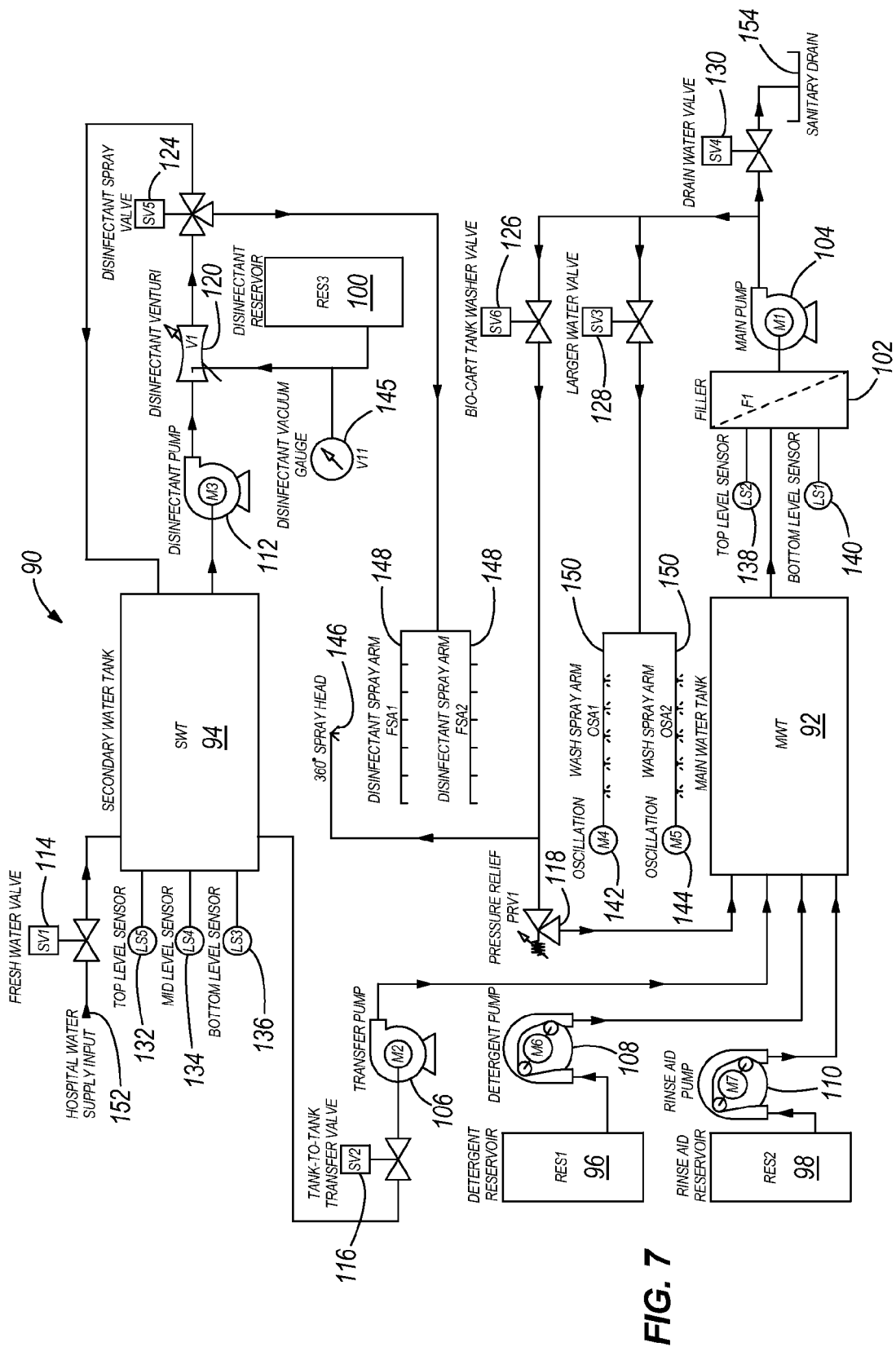
FIG. 7 is a schematic illustration of a fluid system according to one embodiment of the invention for use with the system of FIG. 1.

FIG. 7 illustrates one embodiment of a fluid system 90 for use with the washer system 10 of FIG. 1. The fluid system 90 can include a main water tank 92, a secondary or auxiliary water tank 94, a detergent reservoir 96, a rinse aid reservoir 98, a disinfectant reservoir 100, and a filter 102. The fluid system 90 can also include a main pump 104, a transfer pump 106, a detergent pump 108, a rinse aid pump 110, and a disinfectant pump 112. The fluid system 90 can further include a fresh water valve 114, a tank-to-tank transfer valve 116, a pressure relief valve 118, a disinfectant venturi valve 120, a disinfectant spray valve 124, a bio-cart tank washer valve 126, a large water valve 128, and a drain water valve 130. In addition, the fluid system 90 can include a first top level sensor 132, a mid level sensor 134, a first bottom level sensor 136, a second top level sensor 138, and a second bottom level sensor 140. The fluid system 90 can also include a first motor 142 and a second motor 144. The fluid system can include a disinfectant vacuum gauge 145. The fluid system can further include a spray head 146, disinfectant spray arms 148, and cleaning spray arms 150. Finally, the fluid system 90 can include a supply input 152 and a sanitary drain output 154.

Water enters the fluid system 90 from the supply input 152, which can be a hospital water supply or another suitable water supply (even if that water is not sterile). For example, non-sterile water from a military field hospital or a natural disaster site can be mixed with additives before being used in the fluid system 90. The water passes through the fresh water valve 114, which can be regulated by a control system 200 (as shown and described with respect to FIGS. 9-12). The water can then flow into the secondary water tank 94. The secondary water tank 94 can fill up with the first bottom level sensor 136, the mid level sensor 134, and the first top level sensor 132, respectively, sensing the water level as it rises. The sensors 132, 134, and 136 can send signals to the control system 200. Water can flow from the secondary water tank 94 to the main water tank 92 through the tank-to-tank transfer valve 116 (which can be regulated by the control system 200) via the transfer pump 106. In some embodiments, the washer system 10 can automatically perform a wash cycle while substantially simultaneously filling the secondary water tank 94 for a subsequent wash cycle. In some embodiments, the secondary water tank 94 can be substantially continuously filled and a rapid drain cycle can be operated to increase cycle times. In some embodiments, the washer system 10 can clean and/or disinfect up to ten stretchers per hour or 50 IV poles per hour due in part to the substantially continuous filling of the secondary water tank 94.

Water can also flow from the secondary water tank 94 to the disinfectant venturi 120 via the disinfectant pump 112. Disinfectant can also flow into the disinfectant venturi 120 from the disinfectant reservoir 100, and this flow can be regulated by the disinfectant vacuum gauge 145 and the control system 200. At the disinfectant venturi valve 120 (which can be regulated by the control system 200), the water can be mixed with disinfectant (and possibly air) to achieve a particular pressure before being directed to the disinfectant spray valve 124 (which can be regulated by the control system 200). From the disinfectant spray valve 124, the fluid mixture can be directed to one or more disinfectant spray arms 148 where it can be emitted through the jets 34 onto the medical equipment.

In addition to water filling the main water tank 92, detergent and rinse aid can be added to the main water tank 92. Detergent can flow from the detergent reservoir 96 via the detergent pump 108 into the main water tank 92. Rinse aid can flow from the rinse aid reservoir 98 via the rinse aid pump 110 into the main water tank 92.

From the main water tank 92, the mixture of water, detergent, and rinse aid (i.e., the cleaning mixture) can flow through the filter 102 via the main pump 104. The level of cleaning mixture in the filter 102 can be sensed and a signal can be sent to the control system 200 by the second top level sensor 138 and the second bottom level sensor 140. The portions of the cleaning mixture that are filtered out by the filter 102 can be disposed of by being directed through the drain water valve 130 into the sanitary drain 154. In some embodiments, the filter 102 can have a filtration surface area greater than about two square feet. In one embodiment, the filter 102 can have a filtration surface area of at least about 35 square feet.

The filtered portions of the cleaning mixture that are suitable for cleaning can be directed through the large water valve 128 (which can be regulated by the control system 200) via the main pump 104 to one or more cleaning spray arms 150. The cleaning spray arms 150 can be oscillated by the motors 142 and 144. In addition, the cleaning mixture can be directed through the bio-cart tank washer valve 126 (which can be regulated by the control system 200) to the spray head 146 in order to spray the cleaning mixture from the ceiling of the enclosure 12 in a spray pattern up to about 360 degrees. In some embodiments, the spray head 146 can be used to clean and/or disinfect biohazard carts and linen carts. The pressure relief valve 118 (which can be regulated by the control system 200) can be used to relieve pressure between the main water tank 92 and the spray head 146.

Figure 8:
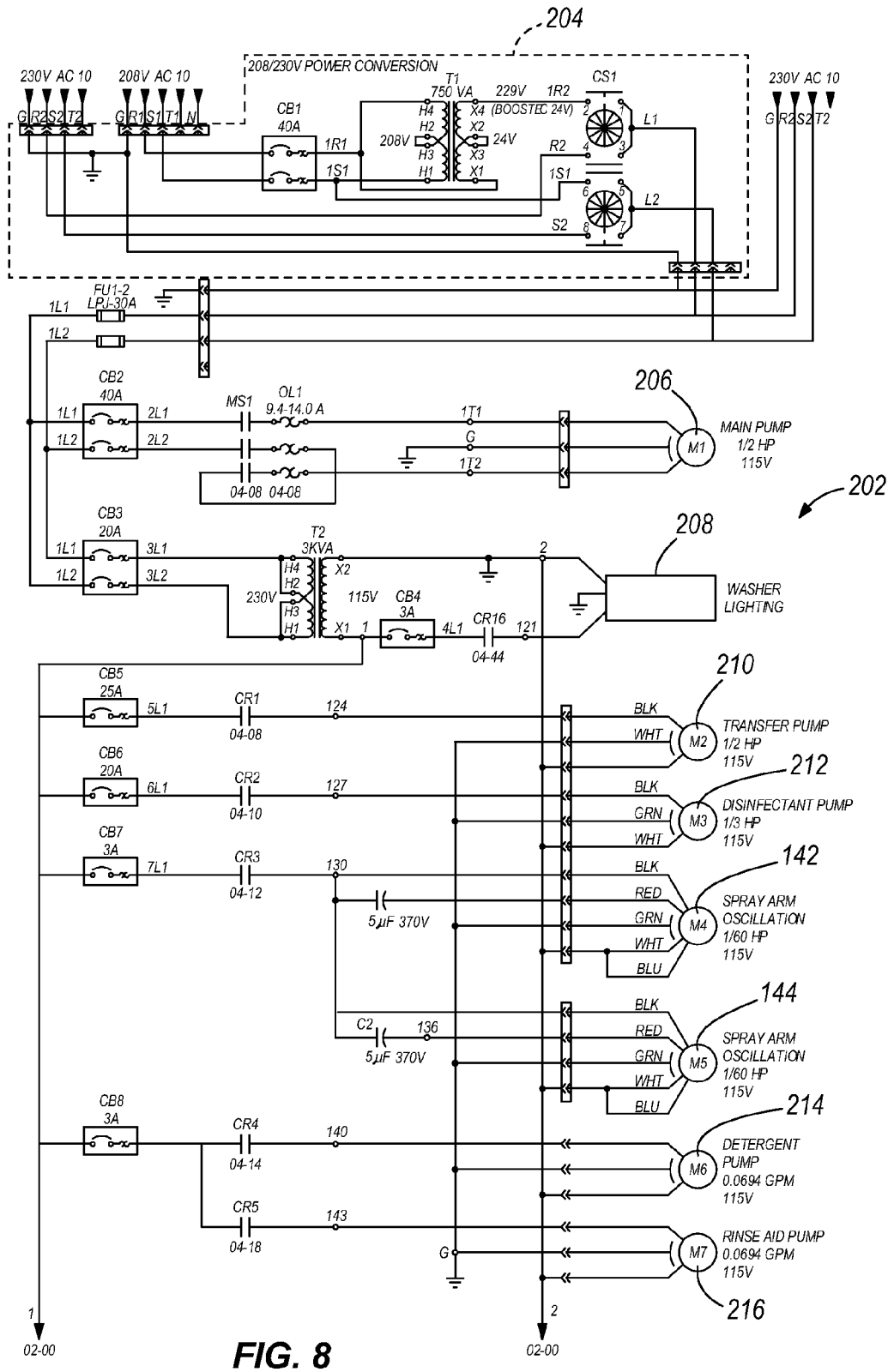
FIG. 8 is a schematic illustration of a power circuit according to one embodiment of the invention for use with the system of FIG. 1.

FIG. 8 illustrates a power circuit 202 that can be used to regulate and provide the appropriate operating currents and voltages to each portion of the fluid system 90. For example, the power circuit 202 can provide power to each motor for each pump and any lighting in the fluid system 90. The power circuit 202 can include a power conversion circuit 204. The power conversion circuit 204 can be connected to a main pump motor 206, washer lighting 208, a transfer pump motor 210, a disinfectant pump motor 212, the motors 142 and 144 that oscillate the cleaning spray arms 150, a detergent pump motor 214, and a rinse aid pump motor 216.

Figure 9:
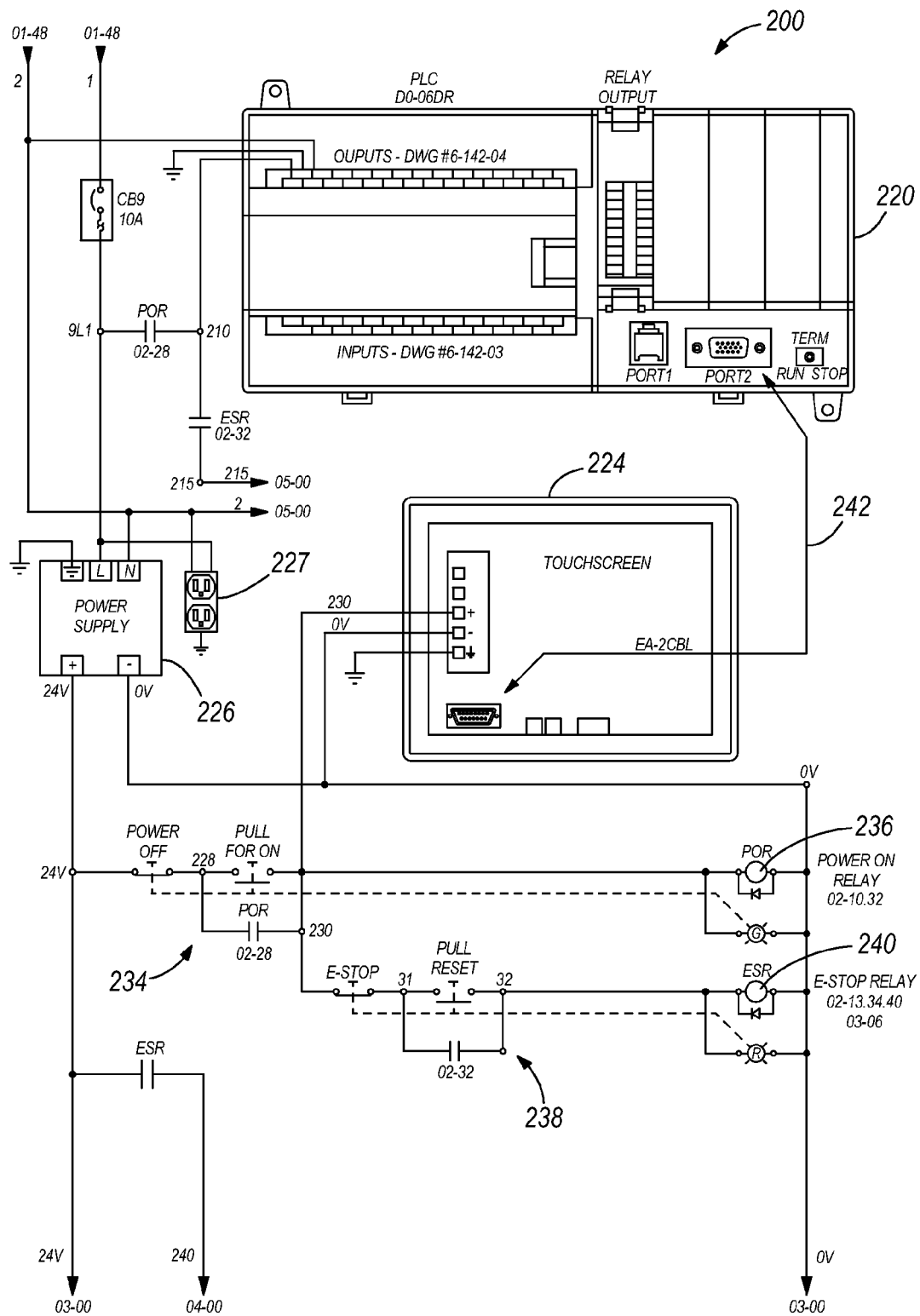
FIG. 9 is a schematic illustration of a control circuit according to one embodiment of the invention for use with the system of FIG. 1.
Figure 10:
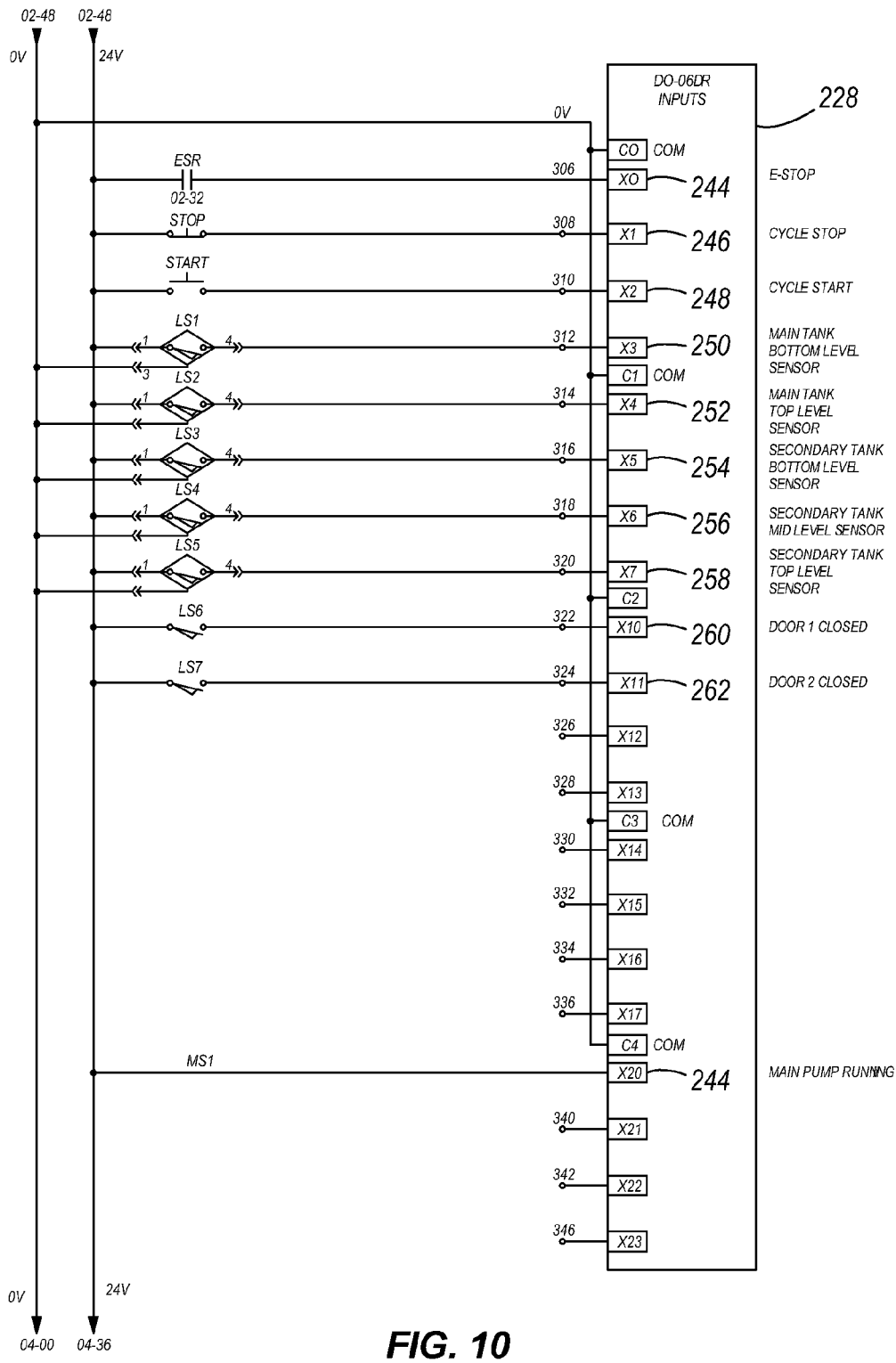
FIG. 10 is a schematic illustration of inputs to the control circuit of FIG. 9.
Figure 11:
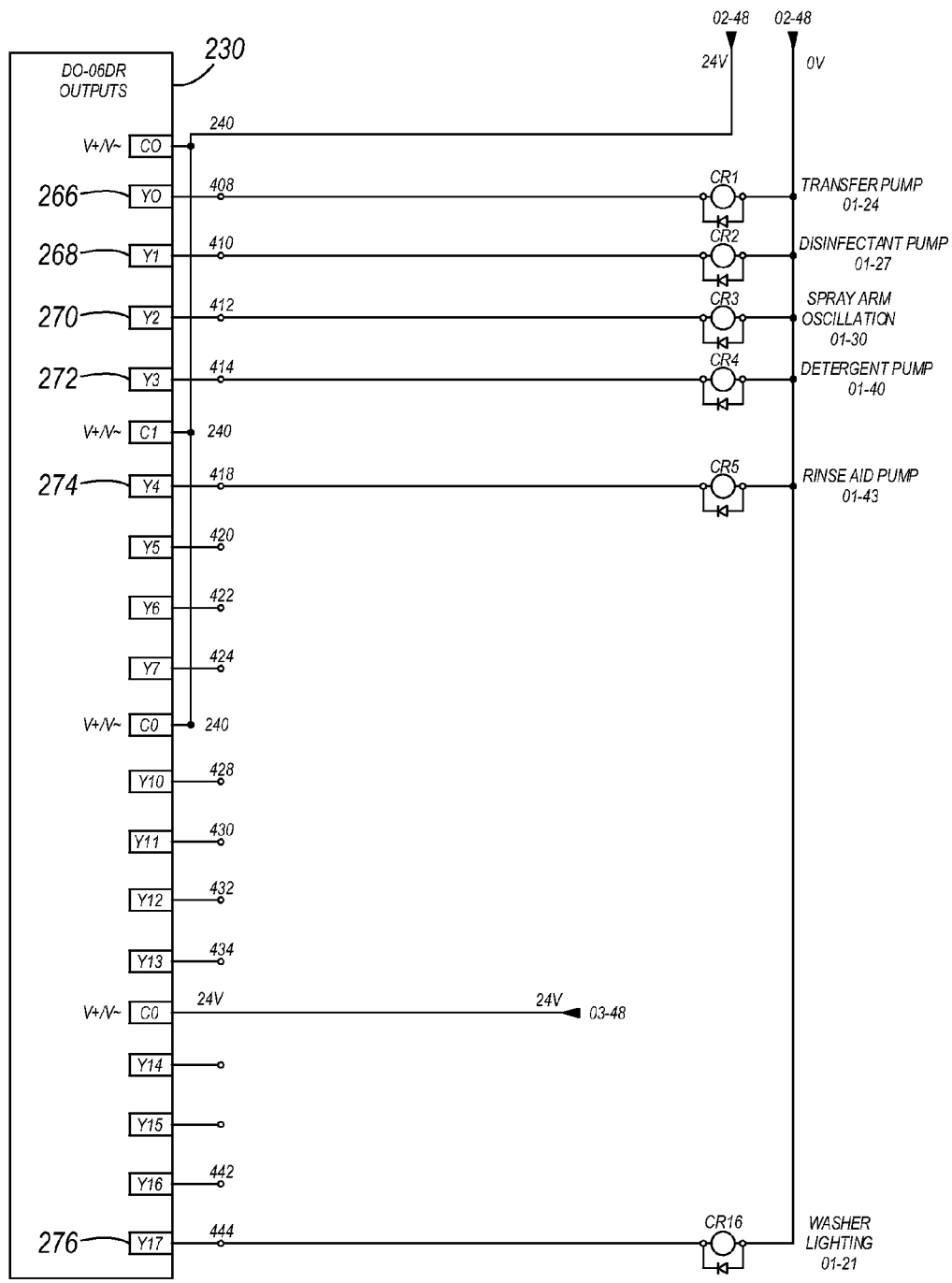
FIG. 11 is a schematic illustration of outputs to the control circuit of FIG. 9.
Figure 12:
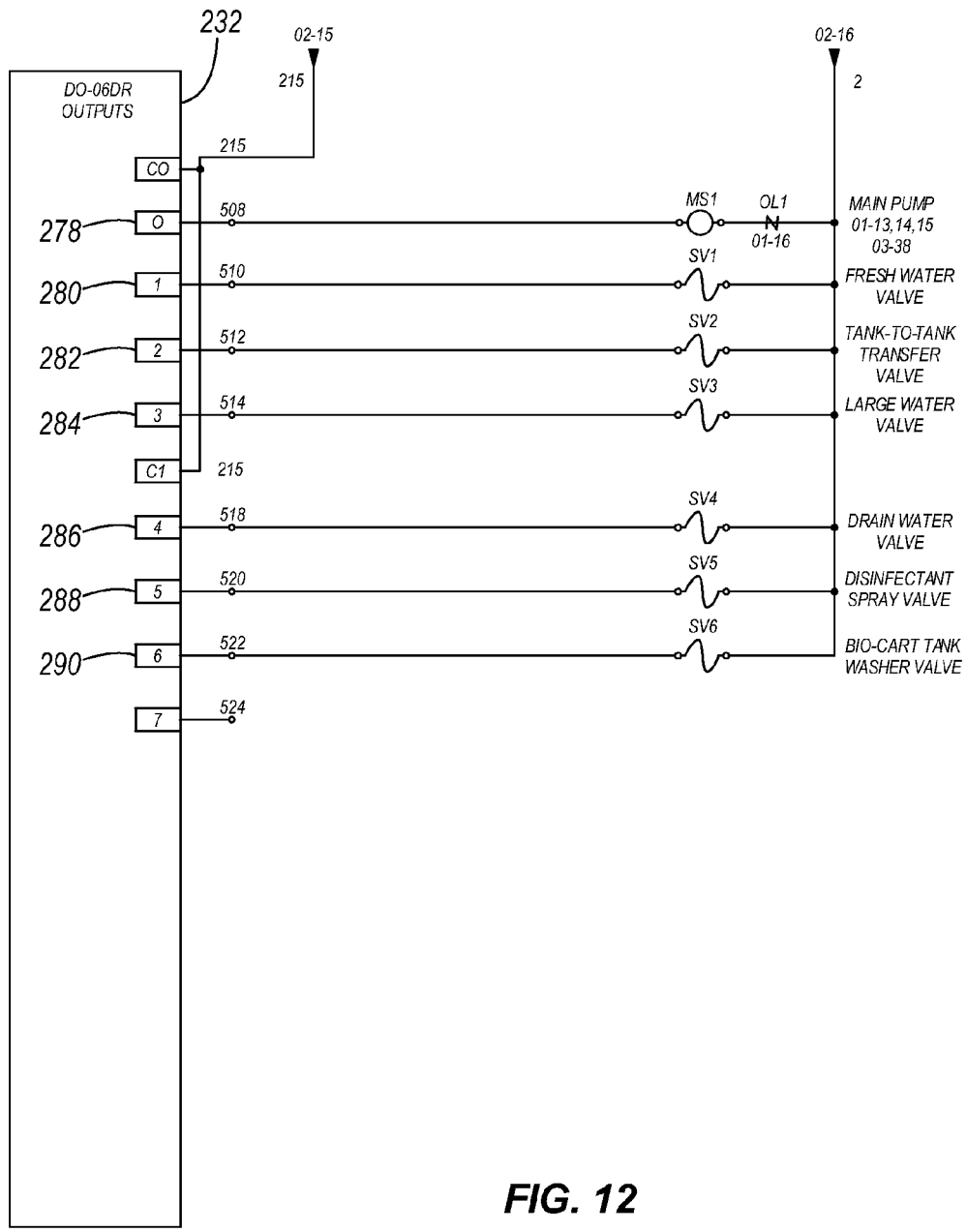
FIG. 12 is a schematic illustration of additional outputs to the control circuit of FIG. 9.

FIGS. 9-12 illustrate the control system 200, which can include a programmable logic controller (PLC) 220, a control panel 224 (which can be a touchscreen, in some embodiments), a power supply 226 (connected to mains power at 227), a set of inputs 228 (as shown in FIG. 10), a first set of outputs 230 (as shown in FIG. 11), and a second set of outputs 232 (as shown in FIG. 12). The PLC 220 can include memory (not shown) for recording and storing a running log for each piece of medical equipment, for example, by documenting one or more of the following: an equipment identification, a personnel name, an equipment location, a wash time, and/or a wash date. In some embodiments, the control system 200 can interface with hospital certification and compliance software. In some embodiments, the control system 200 can also include a code reader (not shown) to read codes (e.g., bar codes or radiofrequency identification codes) placed on pieces of medical equipment. The control system 200 can access the memory to determine whether the pieces of medical equipment have been recently sanitized or require washing. The code reader can be portable, hand-held, and/or wireless.

In some embodiments, the control system 200 can perform a self-cleaning cycle. For example, the self-cleaning cycle can be performed when the washer system 10 is shut down each day. The self-cleaning cycle can be used to clean and disinfect the interior of the enclosure 12, including any equipment racks used that day.

In some embodiments, the control system 200 can operate a cycle to only disinfect medical equipment. For example, the washer system 10 can disinfect medical equipment that is contaminated with Methicillin-resistant *Staphylococcus Aureus*, such as medical equipment from patient isolation rooms.

As shown in FIG. 9, the control system 200 can include a main power control 234 connected to a power-on relay 236 and an emergency stop control 238 connected to an emergency stop relay 240. The control panel 224 can be connected to the PLC 220 by a multi-prong cable, as represented by line 242 of FIG. 9.

As shown in FIG. 10, the set of inputs 228 into the PLC 220 can include one or more of the following: an emergency stop input 244 (corresponding to the emergency stop control 238 of FIG. 8), a cycle stop input 246, a cycle start input 248, a main tank bottom level sensor input 250 (corresponding to the second bottom level sensor 140 of FIG. 7), a main tank top level sensor input 252 (corresponding to the second top level sensor 138 of FIG. 7), a secondary tank bottom level sensor input 254 (corresponding to the first bottom level sensor 136 of FIG. 7), a secondary tank mid level sensor input 256 (corresponding to the mid level sensor 134 of FIG. 7), a secondary tank top level sensor input 258 (corresponding to the first top level sensor 132 of FIG. 7), a first door closed input 260 (corresponding to the position of the first door 16 of FIG. 1), a second door closed input 262 (corresponding to the position of the second door 18 of FIG. 1), and a main pump running input 264 (corresponding to the status of the main pump 104 of FIG. 7).

As shown in FIG. 11, the first set of outputs 230 from the PLC 220 can include one or more of the following: a transfer pump output 266 (to control the transfer pump 106 of FIG. 7 and the transfer pump motor 210 of FIG. 8), a disinfectant pump output 268 (to control the disinfectant pump 112 of FIG. 7 and the disinfectant pump motor 212 of FIG. 8), a spray arm oscillation output 270 (to control the motors 142 and 144 of FIGS. 7 and 8), a detergent pump output 272 (to control the detergent pump 108 of FIG. 7 and the detergent pump motor 214 of FIG. 8), a rinse aid pump output 274 (to control the rinse aid pump 110 of FIG. 7 and the rinse aid pump motor 216 of FIG. 8), and a washer lighting output 276 (to control the washer lighting 208 of FIG. 8).

As shown in FIG. 12, the second set of outputs 232 from the PLC 220 can include one or more of the following: a main pump output 278 (to control the main pump 104 of FIG. 7 and the main pump motor 206 of FIG. 8), a fresh water valve output 280 (to control the fresh water valve 114 of FIG. 7), a tank-to-tank transfer valve output 282 (to control the tank-to-tank transfer valve 116 of FIG. 7), a large water valve output 284 (to control the large water valve 128 of FIG. 7), a drain water valve output 286 (to control the drain water valve 130 of FIG. 7), a disinfectant spray valve output 288 (to control the disinfectant spray valve 124 and/or the disinfectant venturi valve 120 of FIG. 7), and a bio-cart tank washer valve 290 (to control the bio-cart tank washer valve 126 of FIG. 7).

FIG. 13 illustrates cycle steps that can be performed by the control system 200 and the PLC 220 in one embodiment of the invention. Cycle steps 1-4 and 7-12 can be cleaning steps. Cycle step 5 can be a de-liming step. Cycle step 6 can be a tank spray step. Cycle steps 13-14 can be disinfectant steps. Cycle steps 15-25 can be shut-down steps. The following water tanks and sensors are identified in FIG. 13: SWT refers to the secondary water tank 94, MWT refers to the main water tank 92, LS1 refers to the second bottom level sensor 140, LS2 refers to the second top level sensor 138, LS3 refers to the first bottom level sensor 136, LS4 refers to the mid level sensor 134, LS5 refers to the first top level sensor 132, LS6 refers to the first door 16 being closed, and LS7 refers to the second door 18 being closed. The following motors are also identified in FIG. 13: M1 refers to the main pump motor 206, M2 refers to the transfer pump motor 210, M3 refers to the disinfectant pump motor 212, M4 and M5 refer to the oscillating spray arm motors 142 and 144, M6 refers to the detergent pump motor 214, M7 refers to the rinse aid pump motor 216. In addition, the following valves are identified in FIG. 13: SV1 refers to the fresh water valve 114, SV2 refers to the tank-to-tank transfer valve 116, SV3 refers to the large water valve 128, SV4 refers to the drain water valve 130, SV5 refers to the disinfectant spray valve 124, and SV6 refers to the bio-car tank washer valve 126.

In one embodiment of the invention, the cycle steps of FIG. 13 can be performed according to the following description. In cycle step 1, the control system 200 fills the secondary water tank 94 by opening the fresh water valve 114 until the first top level sensor 132 senses the water level in the secondary water tank 94. In cycle step 2, the control system 200 starts filling the main water tank 92 by opening the tank-to-tank transfer valve 116 and turning on the transfer pump 106 for a predetermined time delay. In cycle step 3, the control system 200 adds detergent to the main water tank 92 by turning on the transfer pump 106 and the detergent pump 108 and by leaving the tank-to-tank transfer valve 116 open for a predetermined timed dosage period. In cycle step 4, the control system 200 continues filling the main water tank 92 until the second top level sensor 138 senses the water level and then turns off the transfer pump 106 and closes the tank-to-tank transfer valve 116. In cycle step 5, the control system 200 adds de-liming agent.

In cycle step 6, the control system 200 sprays cleaning mixture from the spray head 146 by turning on the main pump 104 and the bio-cart tank washer valve 126 for a predetermined tank spray time period. In cycle step 7, the control system 200 sprays cleaning mixture from the oscillating spray arms 150 by turning on the main pump 204, turning on the oscillating spray arm motors 142 and 144, and opening the large water valve 128 for a predetermined wash time period. In cycle step 8, the control system 200 drains the main water tank 92 by leaving the main pump 104 on and by opening the drain water valve 130 until the second bottom level sensor 140 no longer senses the water level in the main water tank 92. In cycle step 9, the control system 200 starts filling the main water tank 92 again by turning on the transfer pump 106 and by opening the tank-to-tank transfer valve 116 for a predetermined time delay. In cycle step 10, the control system 200 adds rinse aid to the main water tank 92 by leaving the transfer pump 206 on, by turning on the rinse aid pump 110, and by leaving the tank-to-tank transfer valve 116 open for a predetermined timed dosage period. In cycle step 11, the control system 200 finishes filling the main water tank 92 until the second top level sensor 138 senses the water level in the main water tank 92 and then turns off the transfer pump 106 and closes the tank-to-tank transfer valve 116. In cycle step 12, the control system 200 sprays rinsing fluid by turning on the main pump 104, turning on the motors 142 and 144 for the oscillating spray arms 150, and opening the large water valve 128 for a predetermined rinse time period. In cycle step 13, the control system 200 partially drains the main water tank 92 by leaving the main pump 104 on and by opening the drain water valve 130 for a predetermined drain time period.

In cycle step 14, the control system 200 sprays disinfecting fluid by turning on the disinfectant pump 112 and by opening the disinfectant spray valve 124 for a predetermined disinfectant time period or until the water level falls below the second top level sensor 138 of the main water tank 92. In cycle step 15, the control system 200 substantially or completely drains the main water tank 92 by leaving the main pump 104 on, by closing the fresh water valve 114, and by opening the drain water valve 130 until the water level falls below the second bottom level sensor 140 in the main water tank 92. In cycle step 16, the control system 200 starts draining the secondary water tank 94 by turning on the transfer pump 106 and by opening the tank-to-tank transfer valve 116 until the second top level sensor 138 senses the water level in the main water tank 92. In cycle step 17, the control system 200 substantially or completely drains the water tanks 92 and 94 by turning on the main pump 104 and the transfer pump 106 and by opening the tank-to-tank transfer valve 116 and the drain water valve 130 until the water level falls below both the first bottom level sensor 136 of the secondary water tank 94 and the second bottom level sensor 140 of the main water tank 92. In cycle step 18, the control system 200 partially fills the secondary water tank 94 by opening the fresh water valve 114 until the mid level sensor 134 senses the water level in the secondary water tank 94.

In cycle step 19, the control system 200 adds disinfectant (e.g., Virex® disinfectant manufactured and sold by Johnson Diversey, Inc.) to the secondary water tank 94 by turning on the disinfectant pump 112 and by closing the disinfectant spray valve 124 for a predetermined disinfectant time period. In cycle step 20, the control system 200 starts draining the secondary water tank 94 into the main water tank 92 by turning on the transfer pump 106 and opening the tank-to-tank transfer valve 116 for a predetermined time delay. In cycle step 21, the control system 200 adds detergent to the main water tank 92 by turning on the transfer pump 106, by turning on the detergent pump 108, and by opening the tank-to-tank transfer valve 116 for a predetermined timed dosage period. In cycle step 22, the control system 200 substantially or completely finishes draining the secondary water tank 94 until the water level falls below the first bottom level sensor 136 and then turns off the transfer pump 106 and closes the tank-to-tank transfer valve 116. In cycle step 23, the control system 200 performs a self-cleaning step (e.g., at the end of the day) by turning on the main pump 104, turning on the motors 142 and 144 for the oscillating spray arms 150, and by opening the large water valve 128 for a predetermined shut-down time period. In cycle step 24, the control system 200 substantially or completely drains the main water tank 92 by turning on the main pump 104 and opening the drain water valve 130 until the water level falls below the second bottom level sensor 140 of the main water tank 92 and then closes the fresh water valve 114. At cycle step 25, the cleaning, disinfecting, and/or self-cleaning cycles described above are complete.

Even though the cycle steps are described above in a particular order, the cycle steps can be performed in any suitable order and not all of the cycle steps are necessarily performed in each cycle. For example, disinfect-only cycles can be performed, which do not include the various cleaning and self-cleaning steps described above.

Figure 14A:
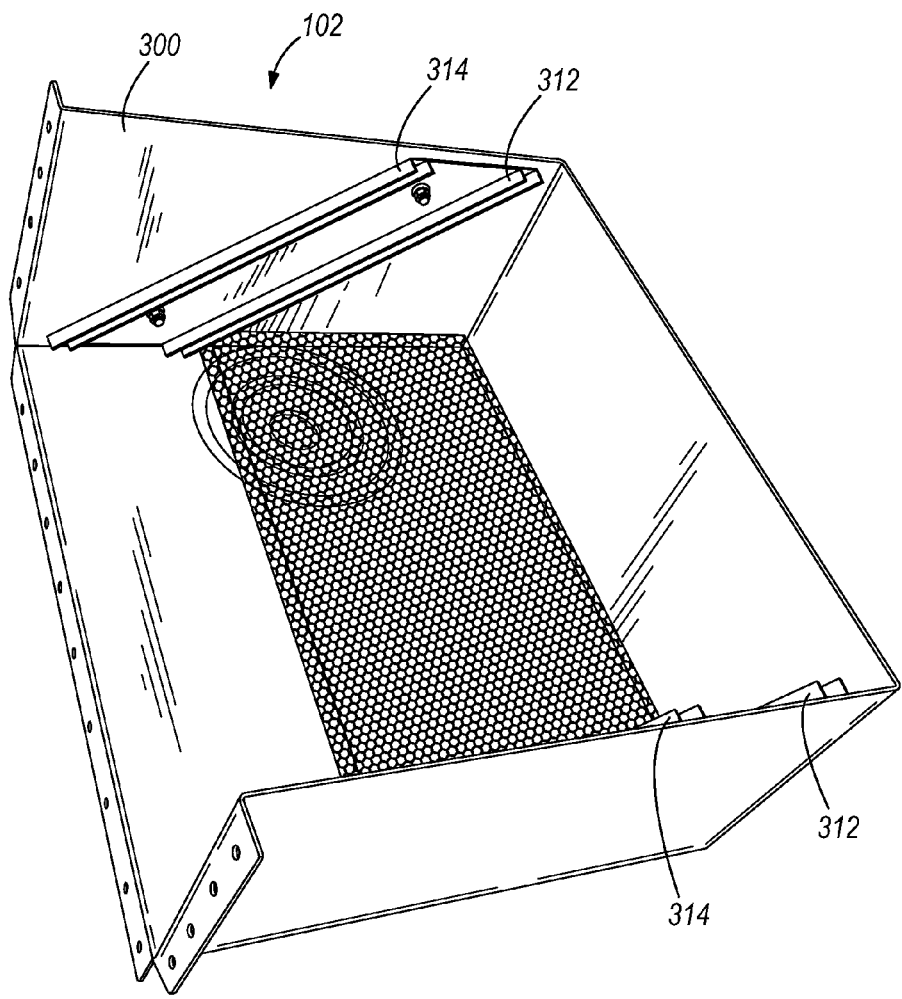
FIGS. 14A, 14B, and 14C are perspective views of a filter according to one embodiment of the invention for use with the system of FIG. 1.
Figure 14B:
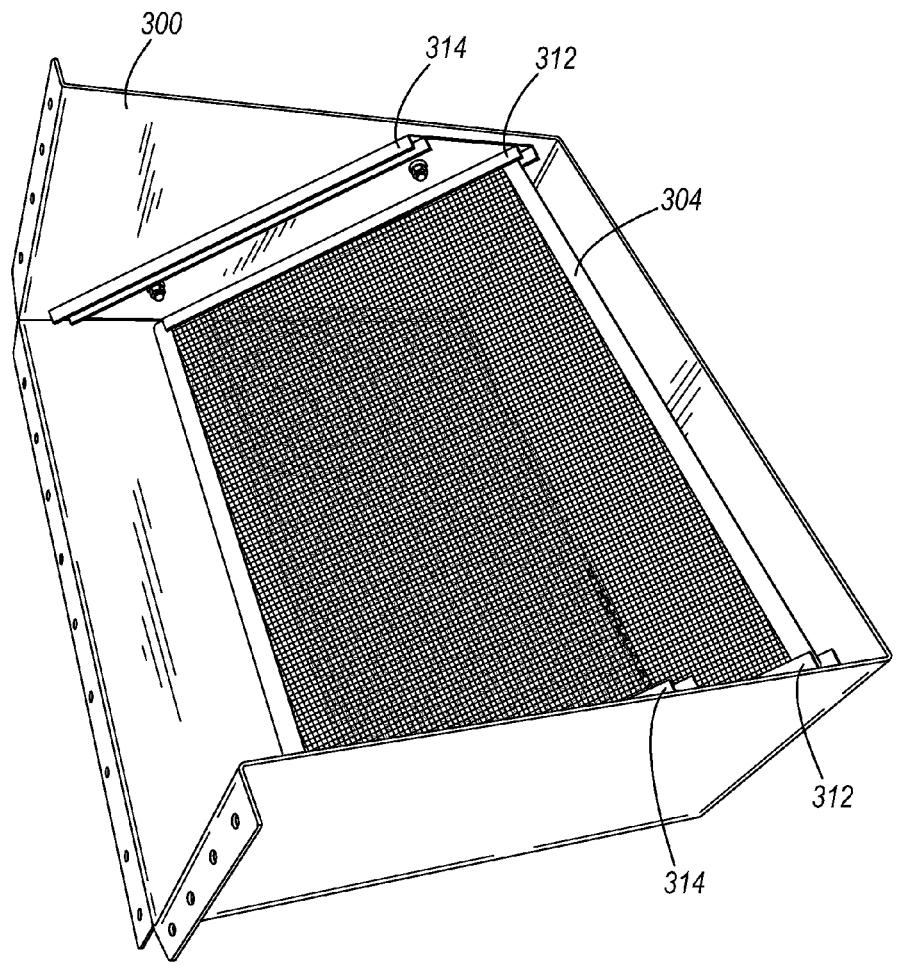
Figure 14C:
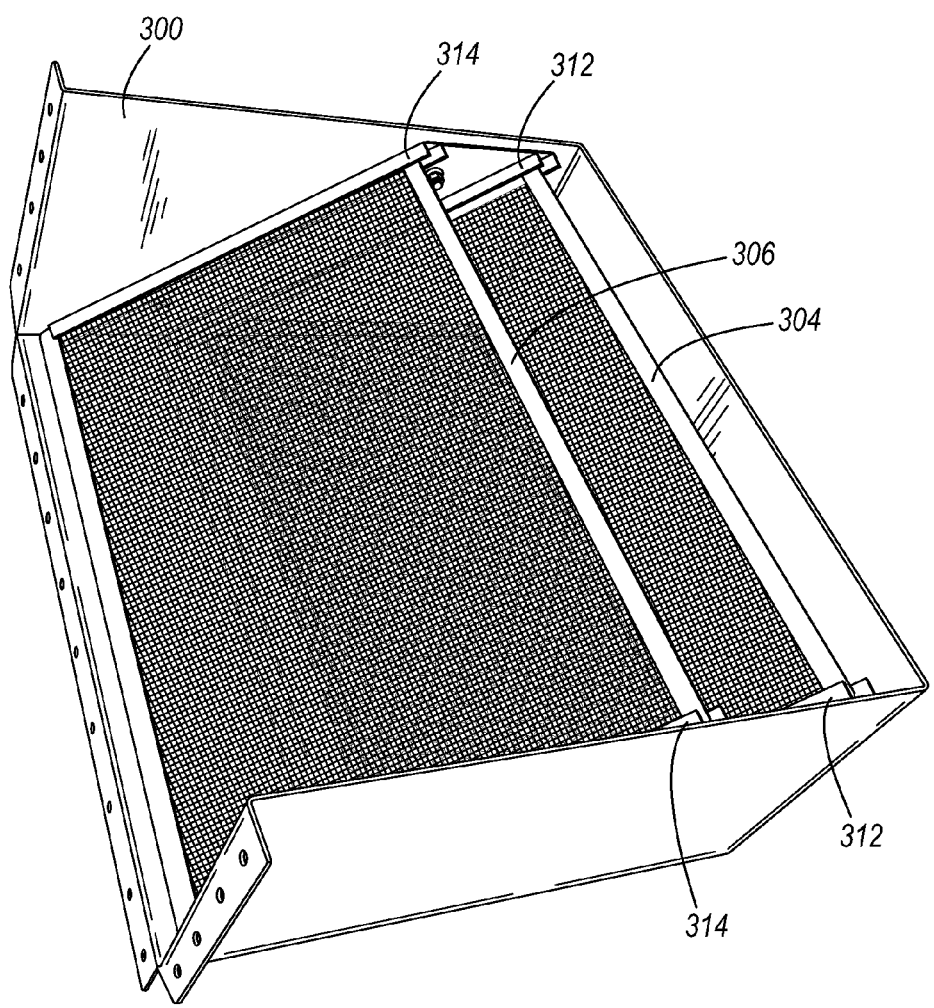

FIGS. 14A, 14B, and 14C illustrate one embodiment of the filter 102 of FIG. 7. The filter 102 can include an enclosure 300, a vortex preventer plate 302, a first filter 304, a second filter 306, an inlet 308, and an outlet (not shown). The enclosure 300 can be rectangular, square, or another suitable shape. The vortex preventer plate 302 can be positioned on one interior side of the enclosure 300 to substantially cover the inlet 308. The vortex preventer plate 302 can include one or more side walls 310 to space the vortex preventer plate 302 from the inlet 308. The vortex preventer plate 302 can help to distribute the cleaning mixture evenly across the first filter 304. As shown in FIG. 14B, the first filter 304 can be positioned within a first set of grooves 312 that can be diagonal with respect to two parallel sides of the enclosure 300. As shown in FIG. 14C, the second filter 306 can be positioned within a second set of grooves 314 that can also be diagonal with respect to two parallel sides of the enclosure 300 and can be spaced from the first set of grooves 312. In one embodiment, the filter 102 of FIGS. 14A, 14B, and 14C can have a filtration surface area of at least about 35 square feet.

Figure 15A:
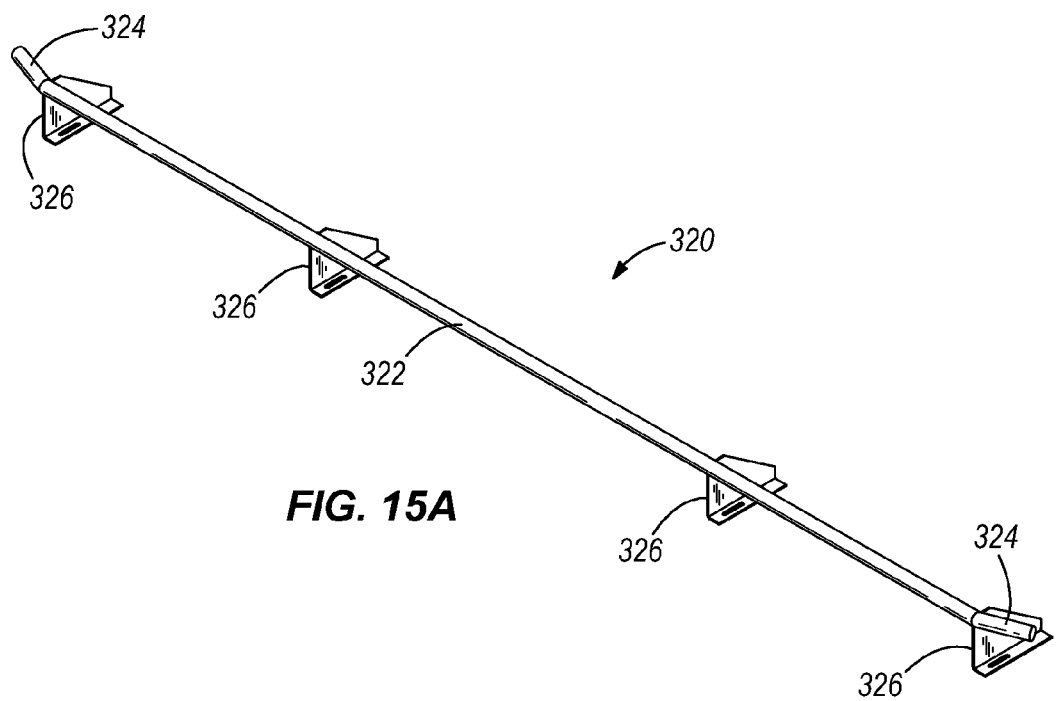
FIGS. 15A and 15B are perspective views of a wheel guide according to one embodiment of the invention for use with the system of FIG. 1.
Figure 15B:
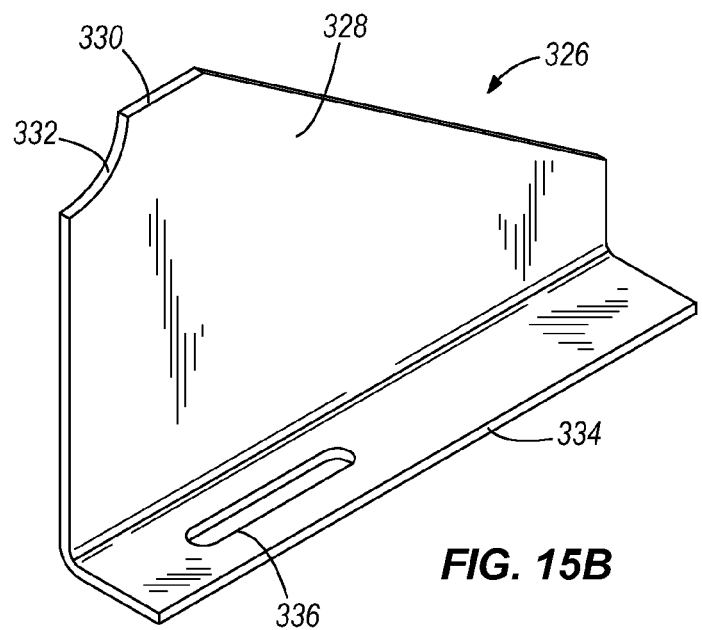

FIGS. 15A and 15B illustrate a wheel guide 320 for use in the enclosure 12 of FIG. 1. One or more wheel guides 320 can be coupled to the floor of the enclosure 12 in order to guide stretchers and IV racks into the enclosure 12. The wheel guide 320 can include an elongated rod 322 with angled ends 324. The wheel guide 320 can also include brackets 326 to support the elongated rod 322 so that the elongated rod 322 is spaced from the floor of the enclosure 12. As shown in FIG. 15B, the bracket 326 can include a triangular portion 328 with a clipped edge 330 that includes a curved recess 332 to support the elongated rod 322. The bracket 326 can also include a flange 334 that can be substantially perpendicular to the triangular portion 328. The flange 334 can include an elongated aperture 336 through which suitable fasteners (not shown) can be positioned and secured to the floor of the enclosure 12.

Figure 16:
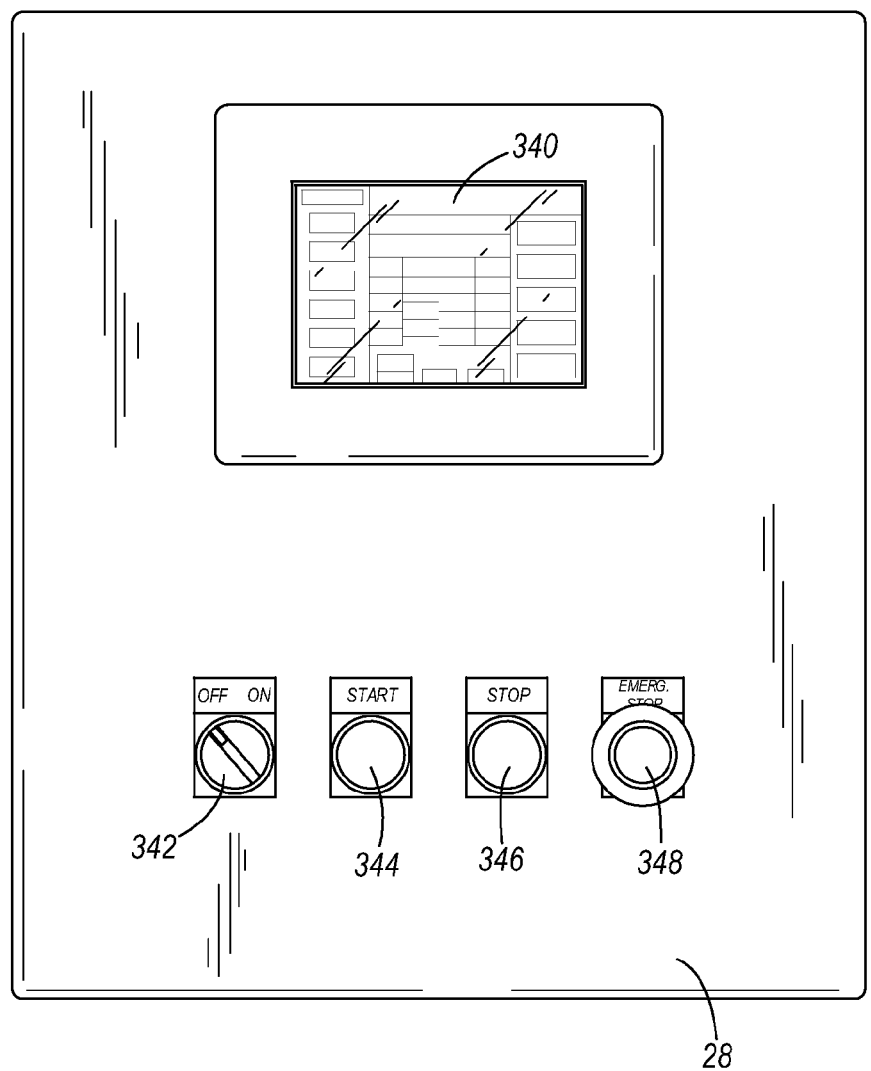
FIG. 16 is a front view of a control panel according to one embodiment of the invention for use with the system of FIG. 1.

FIG. 16 illustrates one embodiment of the control panel 28 of FIG. 1. The control panel 28 can include a screen 340 with a graphical user interface. In some embodiments, the screen 340 can be a touchscreen. In some embodiments, the control panel 28 can include an on/off switch knob 342, a start control knob 344, a stop control knob 346, and an emergency stop control knob 348.

Various features and advantages of the invention are set forth in the following claims.

The invention claimed is:

1. A medical equipment washer for at least one of cleaning and disinfecting medical equipment, the medical equipment washer comprising:
    an enclosure that receives and substantially surrounds the medical equipment, the enclosure including
        a top wall,
        a floor,
        a plurality of side walls, each side wall being connected to the top wall and the floor,
        a first opening in a first one of the side walls, and
        a second opening in a second one of the side walls opposite the first one of the side walls; and
    at least one spray assembly positioned inside the enclosure, the at least one spray assembly automatically emitting fluid to at least one of clean and disinfect the medical equipment, the at least one spray assembly including
        a first supply tube and a second supply tube extending along a third one of the side walls,
        a plurality of stationary arms extending substantially perpendicularly from the first supply tube, each of the stationary arms including at least one nozzle configured to emit a fluid,
        a plurality of movable arms extending substantially perpendicularly from the second supply tube, each of the movable arms including at least one nozzle configured to emit a fluid,
        a third supply tube and a fourth supply tube extending along a fourth one of the side walls,
        a plurality of stationary arms extending substantially perpendicularly from the third supply tube, each of the stationary arms including at least one nozzle configured to emit a fluid,
        a plurality of movable arms extending substantially perpendicularly from the fourth supply tube, each of the movable arms including at least one nozzle configured to emit a fluid;
        a first tank configured to supply fluid to the second supply tube and the fourth supply tube;
        a disinfectant venturi configured to receive fluid and mix the fluid with a disinfectant;
        a secondary tank having a first outlet to supply fluid to the disinfectant venturi, an inlet coupled to a source of unused liquid, and a second outlet for dispensing the unused liquid to the first tank;
        a disinfectant reservoir configured to supply the disinfectant to the disinfectant venturi; and
        a valve coupled to the disinfectant venturi and configured to direct the mixed fluid and disinfectant to one of the secondary tank and the first and third supply tubes.

2. The washer of claim 1 wherein the movable arms are configured to oscillate while emitting fluid.

3. The washer of claim 2 wherein the at least one movable arm oscillates about a swivel joint including at least one annular groove that reduces water pressure on at least one seal.

4. The washer of claim 1 wherein the medical equipment washer automatically performs a wash cycle while substantially simultaneously filling the secondary tank for a subsequent wash cycle.

5. The washer of claim 1 wherein the medical equipment includes at least one of a stretcher, an intravenous pole, a bed, a wheelchair, a linen cart, a biological hazard cart, and a cushion.

6. The washer of claim 1 wherein the medical equipment washer at least one of cleans and disinfects up to about ten stretchers per hour or up to about 50 intravenous poles per hour.

7. The washer of claim 1 and further comprising a control system including memory, the memory storing a running log for each piece of medical equipment documenting at least one of an equipment identification, a personnel name, an equipment location, a wash time, and a wash date.

8. The washer of claim 7 wherein the control system and the memory interface with hospital certification and compliance software.

9. The washer of claim 7 and further comprising a code reader to read codes placed on pieces of medical equipment, the control system accessing the memory to determine whether the pieces of medical equipment have been recently sanitized or require washing.

10. The washer of claim 9 wherein the code reader is at least one of portable, hand-held, and wireless.

11. The washer of claim 1 and further comprising at least one equipment rack positioned inside of the enclosure to support the medical equipment.

12. The washer of claim 11 wherein the at least one equipment rack supports a plurality of intravenous poles.

13. The washer of claim 1 and further comprising a tank washing apparatus coupled to a ceiling of the enclosure.

14. The washer of claim 13 wherein the tank washing apparatus rotates up to about 360 degrees.

15. The washer of claim 13 wherein the tank washing apparatus washes at least one of a biohazard cart and a linen cart.

16. The washer of claim 1 and further comprising a control system that performs a self-cleaning cycle.

17. The washer of claim 16 wherein the control system performs the self-cleaning cycle when the washer is shut down each day.

18. The washer of claim 1 wherein the fluid emitted by the at least one spray assembly is non-sterile water mixed with additives.

19. The washer of claim 18 wherein the non-sterile water is obtained from a military field hospital or a natural disaster site.

20. The washer of claim 1 and further comprising a control system that operates a cycle to only disinfect medical equipment.

21. The washer of claim 1 wherein the washer disinfects medical equipment that is contaminated with Methicillin-resistant *Staphylococcus Aureus*.

22. The washer of claim 1 wherein the at least one spray assembly includes at least one corner-mounted spray arm.

23. The washer of claim 22 wherein the at least one corner-mounted spray arm emits fluid toward an end of a stretcher.

24. The washer of claim 1 and further comprising at least one ramp coupled to the enclosure.

25. The washer of claim 24 wherein the at least one ramp is curved to allow loading of a stretcher without damaging a hydraulic under carriage.

26. The washer of claim 1 wherein the enclosure includes a first door opening on a first end and a second door opening on a second end so that medical equipment can be moved in a single direction through the enclosure.

27. The washer of claim 26 and further comprising a control panel centrally located between the first door opening and the second door opening.

28. The washer of claim 1 and further comprising a control system that operates to continuously fill at least one secondary tank and operates a rapid drain cycle to at least one of decrease cycle times and increase the number of cycles per hour.

29. The washer of claim 1 wherein the enclosure and the at least one spray assembly are constructed of a material including stainless steel.

30. The washer of claim 1 wherein the enclosure has a maximum width of about four feet in order to fit through a standard hospital door.

31. The washer of claim 1 and further comprising a filtration system having a filtration surface area greater than about two square feet.

32. The washer of claim 31 wherein the filtration system has a filtration surface area of at least about 35 square feet.

33. The washer of claim 1 wherein the washer can wash medical equipment from one of a hospital, a public health facility, a military field hospital, emergency medical services, a biological terror event, and a mobile unit.

34. The washer of claim 1, further comprising a detergent reservoir configured to supply a detergent to the first tank.

35. The washer of claim 1, further comprising a rinse aid reservoir configured to supply a rinse aid to the first tank.

36. The washer of claim 1, wherein the source of unused liquid is external to the washer.

* * * * *